United States Patent
Lai et al.

(10) Patent No.: US 8,985,768 B2
(45) Date of Patent: Mar. 24, 2015

(54) INTEGRATED REFRACTOR

(71) Applicants: Ming Lai, Dublin, CA (US); Meijuan Yuan, Dublin, CA (US)

(72) Inventors: Ming Lai, Dublin, CA (US); Meijuan Yuan, Dublin, CA (US)

(*) Notice: Subject to any disclaimer, the term of this patent is extended or adjusted under 35 U.S.C. 154(b) by 0 days.

(21) Appl. No.: 13/668,288

(22) Filed: Nov. 4, 2012

(65) Prior Publication Data

US 2013/0135581 A1     May 30, 2013

Related U.S. Application Data

(60) Provisional application No. 61/629,749, filed on Nov. 25, 2011.

(51) Int. Cl.
| | |
|---|---|
| *A61B 3/10* | (2006.01) |
| *A61B 3/02* | (2006.01) |
| *A61B 3/18* | (2006.01) |

(52) U.S. Cl.
CPC ............... *A61B 3/18* (2013.01); *A61B 3/1015* (2013.01)
USPC .......................................... 351/205; 351/239

(58) Field of Classification Search
CPC ............................ A61B 3/0075; A61B 3/1015
USPC ........................................... 351/204, 205, 239
See application file for complete search history.

(56) References Cited

U.S. PATENT DOCUMENTS

| | | |
|---|---|---|
| 5,617,157 A | 4/1997 | Shalon et al. |
| 6,382,795 B1 | 5/2002 | Lai |
| 6,406,146 B1 | 6/2002 | Lai |
| 6,575,572 B2 | 6/2003 | Lai et al. |
| 7,237,898 B1* | 7/2007 | Hohla et al. .......... 351/246 |
| 7,425,067 B2 | 9/2008 | Warden et al. |
| 7,909,461 B2 | 3/2011 | Warden et al. |
| 2005/0241653 A1 | 11/2005 | Van Heugten et al. |
| 2005/0243276 A1 | 11/2005 | Van Heugten et al. |
| 2008/0100800 A1* | 5/2008 | Guillen et al. ............ 351/205 |
| 2009/0073384 A1* | 3/2009 | Warden et al. ............ 351/221 |

* cited by examiner

*Primary Examiner* — Mahidere Sahle

(57) ABSTRACT

The present invention contemplates a refraction system to integrate the objective and subjective measurement into a single instrument. The present invention also contemplates a refraction system with open-field and binocular viewing to overcome instrument myopia and to mimic viewing experience of a phoropter. The present invention further contemplates a refraction system employing a pair of optical trombones to eliminate the need of flipping plurality sets of trial lenses for defocus power correction.

20 Claims, 5 Drawing Sheets

INTEGRATED REFRACTOR

This application claims the benefit of U.S. Provisional Application No. 61/629,749, filed on Nov. 25, 2011.

1. RELATED FIELD

The invention relates to a method and device for measuring optical aberrations and refractive errors of a human eye. In particular, the invention relates to a method and device for measuring optical aberrations and refractive errors of a human eye via a single instrument integrated objective and subjective measurements, implemented open-field viewing, binocular, and optical relay of unit magnification, and employed an interactive closed-loop configuration for measurement and correction.

2. BACKGROUND

Auto-refractor and phoropter are commonly used for providing refraction prescription for eyeglass or contact lenses. An auto-refractor is used to produce objective measurement of eye spherical defocus power, cylinder power and cylinder axis. A phoropter is used to refine the measurement of auto-refractor through subjective response from the patients. The auto-refractor and phoropter are typically stand-alone instruments, and they require different sitting and alignment to perform the measurements. Also, a phoropter displays a number of trial lenses along the viewing path of each subject eye, and relies on response from the patient to identify the optimal refraction correction and thus the patient's prescription. Typically it takes 10 to 30 minutes to make a thorough refraction measurement with the common practices of auto-refractor and phoropter.

An auto-refractor typically measures one eye at a time and directs the subject eye looking at a fixation target inside the instrument. Instrument myopia, due to accommodating and fixating at an internal target, is commonly an issue limiting measurement accuracy and reliability.

An auto-phoropter is a good advancement from a phoropter, equipped with a control box and motorized mechanism to change trial lenses. An auto-phoropter is basically a motorized phoropter, which employs multiple sets of trial lenses to produce refraction correction for sphere and astigmatism. The measurement procedure via auto-refractor and auto-phoropter is still elaborating and time consuming.

3. SUMMARY

The present invention contemplates a refraction system to integrate the objective and subjective measurement into a single instrument. The present invention also contemplates an open-field and binocular viewing to overcome instrument myopia and to mimic viewing experience of a phoropter. The present invention further contemplates an optical relay with unit magnification to eliminate the need of flipping plurality sets of trial lenses for defocus correction. Furthermore, the present invention contemplates an integrated refractor having an axial dimension as thin as a convention phoropter so as to mimic the viewing experience of a phoropter.

Accordingly, a first objective of the present invention is to provide a new and improved refraction system integrating objective and subjective measurements into a single instrument.

A second objective of the present invention is to provide a new and improved refraction system overcoming instrument myopia and enabling measurement of accommodation.

A third objective of the present invention is to provide a new and improved refraction system employing a power-adjustable optical relay to eliminate the plurality sets of trial lenses for defocus correction.

A fourth objective of the present invention is to provide a new and improved refraction system having an axial dimension as thin as a convention phoropter so as to mimic the viewing experience of a phoropter.

The above and other objectives and advantages of the invention will become more apparent in the following drawings, detailed description, and claims.

4. DRAWINGS

Figure 3:
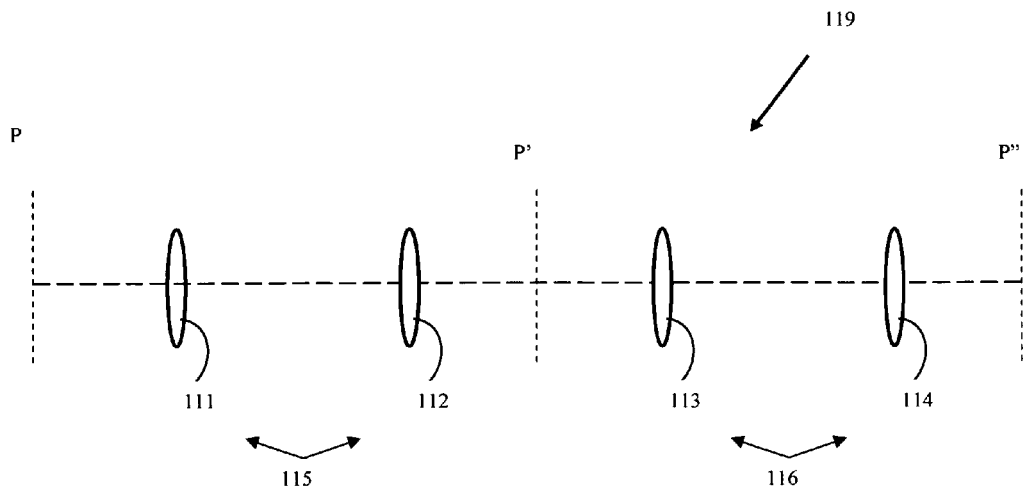
Figure 3A:
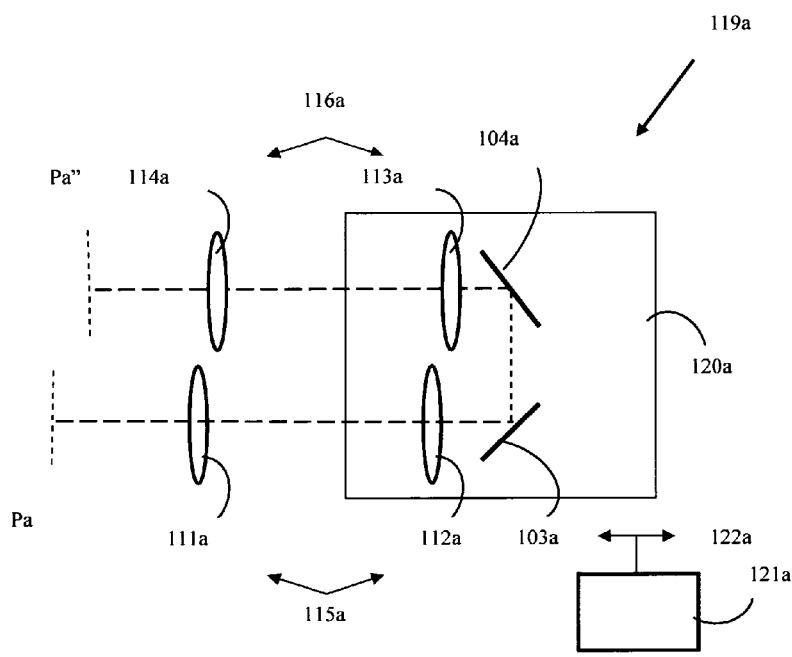
Figure 3B:
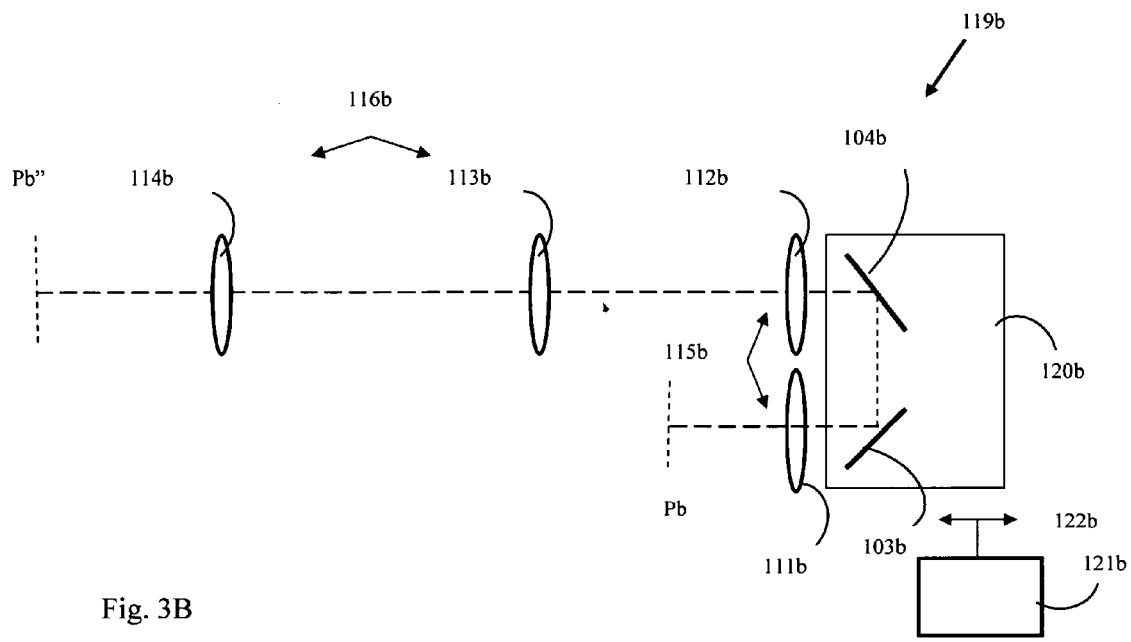
Figure 3C:
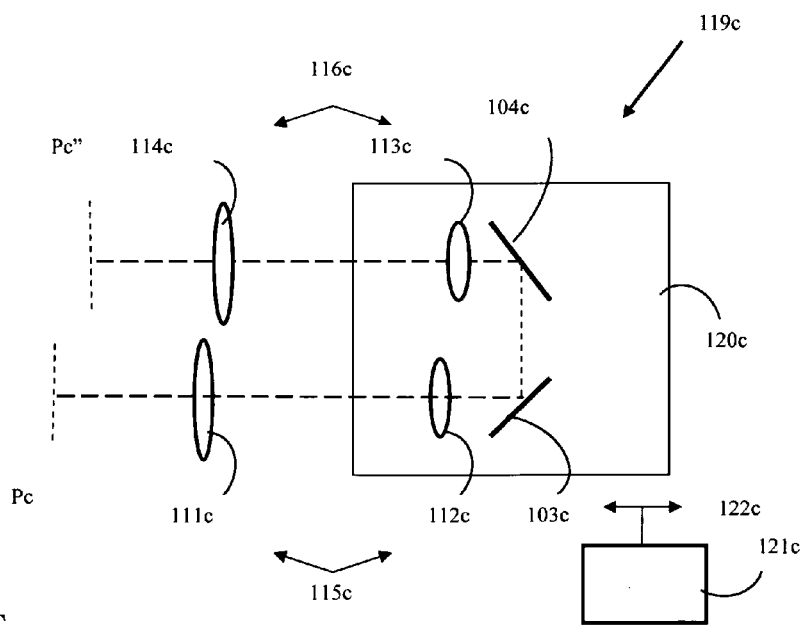
Figure 3D:
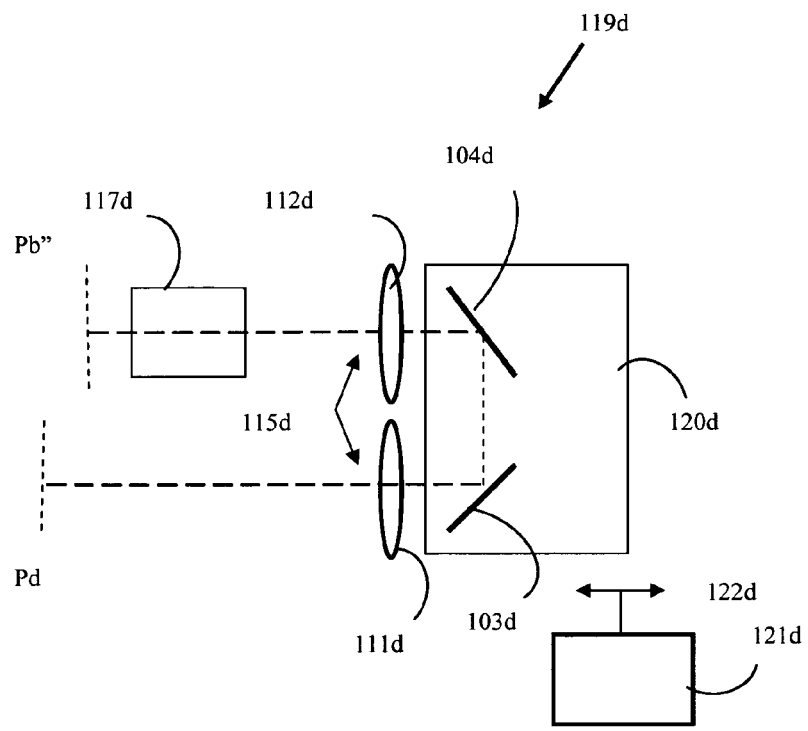

FIG. 3 shows an optical relay of unit magnification, as a preferred embodiment of the present invention. FIG. 3A shows an optical relay of unit magnification consisting of a pair of folded optical trombones; FIG. 3B shows another optical relay of unit magnification in a configuration consisting of an optical trombone and an a focal; FIG. 3C shows further another optical relay of unit magnification in a configuration consisting of a pair of complement optical relay; FIG. 3D shows further another optical relay of unit magnification in a configuration consisting of an optical trombone and an image-reversing prism.

Figure 4:
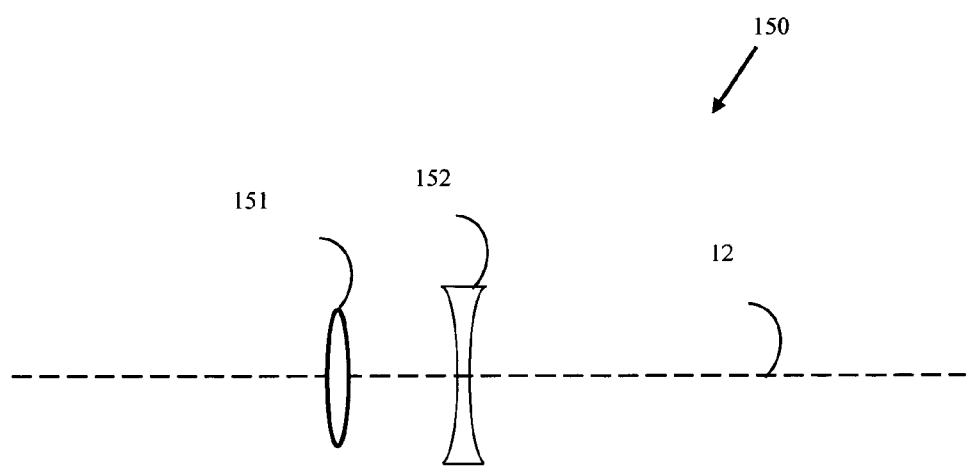

FIG. 4 shows a pair of positive and negative cylinder lenses that produces an effective cylindrical lens of adjustable power and axis.

5. DESCRIPTION

Figure 1:
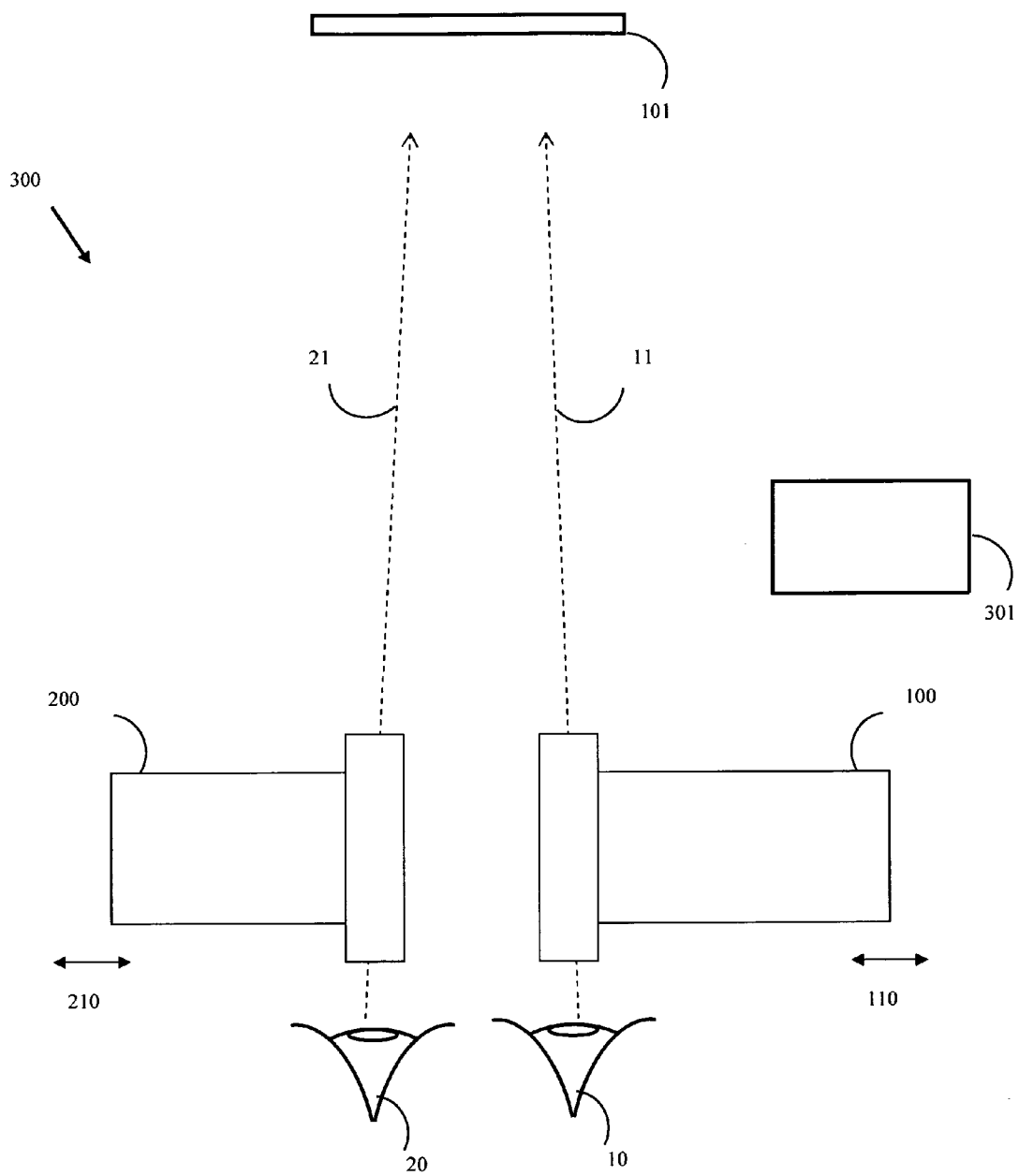
FIG. 1 shows an embodiment of a refraction system implemented with a left and a right viewing unit.

FIG. 1 shows an embodiment of a refraction system 300 implemented with a left viewing unit 200 and a right viewing unit 100, in accordance with the present invention. A left subject eye 20 looks through the left viewing unit 200, along viewing path 21, to fixate on a viewing chart 101. A right subject eye 10 looks through the right viewing unit 100, along viewing path 11, to fixate on the same viewing chart 101. Moving mechanism 210 and 110 are to translate the left viewing unit 200 and the right viewing unit 100 to align with pupils of the left eye 20 and the right eye 10, respectively. The pupil distance between the left eye 20 and the right eye 10 can thus be measured via separation between the left viewing unit 200 and right viewing unit 100.

The viewing chart 101 is, in a preferred embodiment, placed outside the refraction system 300 to provide an open view test and to facilitate elimination of instrument myopia. The left viewing unit 200 and the right viewing unit 100 provide independently defocus corrections and have a unit magnification, i.e. the viewing chart 101 appears the same size and same orientation as with eyeglasses or contact lenses correction. In this application document, a unit magnification refers to a +1 magnification.

In a preferred embodiment, the viewing path 21 appears straight to the left eye 20, and the viewing path 11 appears straight to the right eye 10. The thickness of each viewing unit along the straight viewing path is preferably 100 mm or shorter, such that the viewing experience to the eyes mimics that of a phoropter or auto-phoropter. Such a viewing experience enables near visual acuity test similar to that with a phoropter or auto-phoropter. Such a viewing experience also differentiates the present invention further from various conventional auto-refractors, wavefront aberrometers, and subjective refractors.

The viewing chart 101 is positioned at a predetermined distance from the subject eyes 10 and 20. The viewing chart 101 is preferably positioned 20 feet (6 meters) away from the eye 10 for distance visual acuity test, and 40 cm away for near visual acuity test.

The refraction system 300 also includes a system processor 301, which is coupled electronically to the left viewing unit 200 and the right viewing unit 100 to perform system control, to process measurement data, and to calculate prescription for eyeglasses and contact lenses. As shown in figures below, the refraction system 300 implements continuous adjustments of defocus power and astigmatism and thus is capable to provide prescription with precision and accuracy higher than the industrial standard of eyeglasses and contact lenses, i.e., 0.25 D in sphere and cylinder power and 1 degree in cylinder axis.

A software algorithm of the system processor 301 is to round off and to convert the initial prescription to precision steps of the industrial standard and to provide this standardized prescription for conventional eyeglasses and contact lenses. In a preferred embodiment, the initial prescription of high precision is provided in a different, non-conventional format for fabricating custom or premium eyeglasses or contact lenses. This initial prescription of high precision can be coded and used for specific lens fabrication process.

Figure 2:
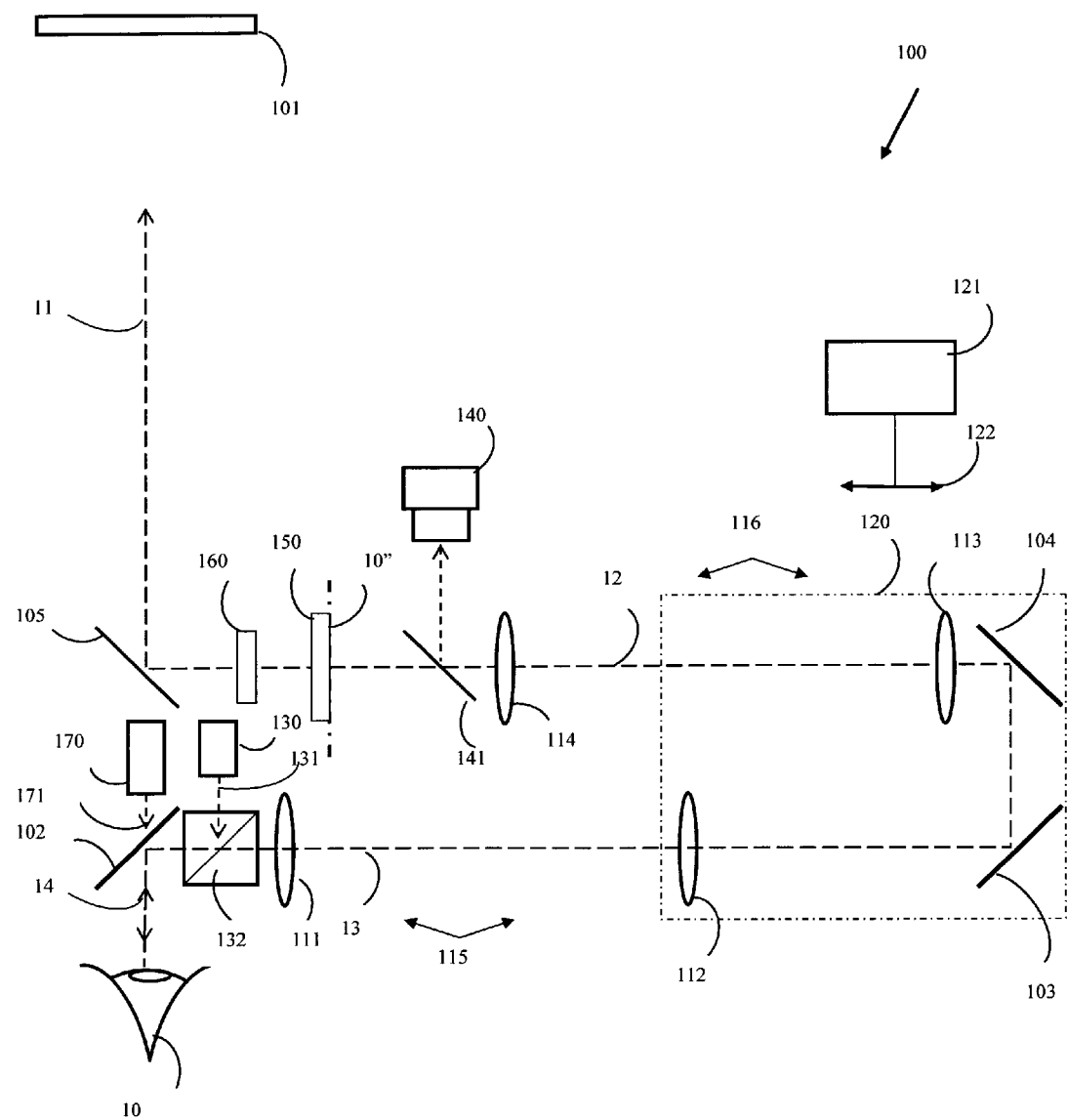
FIG. 2 shows optical layout of the right viewing unit, in accordance with an embodiment of the present invention.

FIG. 2 shows an optical layout of the right viewing unit 100, in accordance with an embodiment of the present invention. The straight viewing path 11 is folded with turning mirrors 102-105. Lenses 111-112 form an optical trombone 115 and lenses 113-114 forms another optical trombone 116. Lenses 111-114 can be identically in focal length, and the pair of optical trombones 115-116 produces a unit magnification, i.e., +1 magnification. The turning mirrors 103-104 and the lenses 112-113 are mounted on a translation stage 120. A moving mechanism 121 drives the stage 120 moving along direction 122 to change defocus power of the pair of optical trombones 115-116.

A cylinder corrector 150 is inserted into the beam path 12 to correct cylindrical errors of the subject eye 10. The cylinder corrector 150 may consists of a set of cylindrical lenses or a pair of positive and negative lenses. The construction and alignment of a cylinder corrector 150 are known to those skilled in the art.

A probe beam generator 130 injects a probe beam 131 via a polarized beam splitter 132 into the beam path 13 and then into the eye 10. Scattered light of the probe beam 131 from the retina of eye 10 is relayed via the pair of optical trombone 115-116 and directed via a dichromic mirror 141 into a refractor sensor 140, which measures refraction errors of the eye 10. The measurement outcome from the refractor sensor 140 is used to drive the moving mechanism 121 to correct defocus error of the eye 10. The measurement outcome from the refractor sensor 140 is also used to drive the cylinder corrector 150 to correct cylindrical error of the eye 10. The moving mechanism 121 can be adjusted manually or with a motorized mechanism. Also, the cylinder corrector 150 can be adjusted manually or with a motorized mechanism.

A viewing path indicator 170 is positioned along the straight viewing path 11 for the eye 10 to align with the straight viewing path 11. The indicator 170 can be formed with a visible LED. The indicator 170 may have different color for the left viewing unit 200 and the right viewing unit 100 such that easy judgment can be made whether both eyes are aligned with their corresponding viewing paths 21 and 11.

A viewing path blocker 160 is positioned along the beam path 12 to block or unblock the eye 10 from looking through the viewing unit 100. With the viewing path blocker 160, one eye can be measured naturally without the influence from the other eye.

The refractor sensor 140 can be a wavefront sensor, such as a Hartmann-Shacksensor or a Moiré sensor. The refractor sensor 140 measures refraction errors of the eye 10 through the optical relay, e.g., the pair of optical trombones 115-116. When the pair of optical trombones 115-116 is adjusted to compensate for the eye defocusing, the refractor sensor 140 may be used to measure the residual aberrations between the eye aberrations and the defocusing compensation.

The pair of optical trombones 115-116 is simply a preferred embodiment of an optical relay that provide defocus compensation and unit magnification. The optical relay 115-116 of unit magnification also introduces a conjugated plane 10" of the eye 10 and enables cylinder corrector 150 to place at a plane optically equivalent to that of eyeglass or contact lenses.

To mimic the viewing experience of a phoropter or an auto-phoropter, the viewing path 14 is preferably collinear with the viewing path 11, and the distance between the first turning mirror 102 and the last turning mirror 105 is preferably 100 mm or shorter. The viewing chart 101 is preferably positioned 20 feet (6 meters) away from the eye 10 for distance visual acuity test, and 40 cm away for near visual acuity test.

Preferably, the viewing distance to the viewing chart 101 from the eye 10 is equal to that from the conjugated plane 10". This way the viewing chart 101 appears to the eye 10 equivalent to direct viewing from viewing path 14 through viewing path 11.

FIG. 3 shows an optical relay 119 of unit magnification, as a preferred embodiment of the present invention. Preferably, the two relay stages 115-116 are a pair of optical trombones that collectively produces a unit optical relay. The lenses 111-114 can be identical in focal length f. Pupil plane P is one focal length f away from the first lens 111. The distance between lenses 112 and 113 is fixed to twice the focal length, 2f. Conjugate plane P'" locates one focal length f away from the last lens 114. Conjugated plane P'" has a unit magnification, i.e., +1 magnification, with respect to the pupil plane P. Optical power of the optical relay 119 varies with the separation between lenses 111-112 and the separation between lenses 113-114.

FIG. 3A shows an optical relay 119a of unit magnification consisting of a pair of folded optical trombones 115a and 116a. Turning mirrors 103a-104a and lenses 112a-113a are mounted on a translation 120a. As a pair of optical trombones, the separation between lenses 111a-112a and the separation between lenses 113a-114a can be adjusted simultaneously with a moving mechanism 121a. Consequently, Optical power of the optical relay 119a can be adjusted with the translation 120a, via a moving mechanism 121a along moving direction 122a.

FIG. 3B shows another optical relay 119b of unit magnification in a configuration consisting of an optical trombone 115b and an afocal 116b. The lenses 111b-114b can also be identically in focal length. Turning mirrors 103b-104b are mounted on a translation 120b. In such a configuration, the optical separation between lenses 111b-112b is adjustable with a moving mechanism 121b along moving direction 122b, while the separation between lenses 113b-114b remains constant and is twice of the focal length.

FIG. 3C shows further another optical relay 119c of unit magnification in a configuration consisting of a pair of complement optical relay 115c and 116c. In this embodiment, lenses 112c-113c are identical with a focal length f1, and lenses 111c and 114c are identical but with a different focal length f2. That is, the optical relay 115c has a magnification of x and the other optical relay 116c has a magnification of 1/x.

Turning mirrors 103c-104c and lenses 112c-113c are mounted on a translation 120c. To introduce a defocus power correction, the separation between lenses 111c-112c and the separation between lenses 113c-114c can be adjusted simultaneously with a moving mechanism 121c along moving direction 122c.

FIG. 3D shows further another optical relay 119d of unit magnification in a configuration consisting of an optical trombone 115d and an image-reversing prism 117. The image-reversing prism 117 can be made of a pair of Porro prisms placed at right angles to each other such that the image is rotated and reversed. Porro prism is well known to those skilled in the art.

Turning mirrors 103d-104d are mounted on a translation 120d. In such a configuration, the optical separation between lenses 111d-112d is adjustable with a moving mechanism 121d along moving direction 122d.

FIG. 4 shows a pair of positive 151 and negative 152 cylinder lenses that produces an effective cylindrical lens of adjustable power and axis. The paired cylinder lenses 151-152 forms a cylinder corrector 150. The positive cylinder 151 and negative cylinder 152 can be rotated around the viewing path 12 independently to adjust cylinder power and axis. The construction and operation of a cylinder corrector 150 with paired positive 151 and negative 152 cylindrical lenses is well known to those skilled in the art.

As shown in FIG. 3 and FIGS. 3A-3D, defocus power correction with an optical relay can be made continuously. Lab experiments have demonstrated that, with instrumentation conditions, defocus power correction with an optical relay can be made and measured to an accuracy better than 0.125 D and to a precision better than 0.06 D. Also as shown in FIG. 4, cylinder power correction and axis adjustment can be made continuously. Lab experiments have also demonstrated that, with instrumentation conditions, cylindrical power correction with an optical relay can be made and measured to an accuracy better than 0.125 D and to a precision better than 0.06 D. As a result, the refraction system 300 is capable to provide refraction measurements and prescription substantially more accurate and more precise than the industrial standard with a phoropter or auto-phoropter, i.e., 0.25 D in sphere and cylinder power and 1 degree in cylinder axis.

Besides, the refractor sensor 140 of the refraction system 300 is preferably a wavefront sensor, such as a Hartmann-Shack wavefront sensor or a Moire wavefront sensor. As a result, the refraction system 300 is capable to provide measurement data of wavefront aberrations.

Consequently, refraction system 300 is capable to perform objective and subjective visual acuity test, to provide precise prescription, and to measure wavefront aberrations. On the other hand, the precise prescription can be rounded off and converted to a precision of the industrial standard, i.e., 0.25 D in sphere and cylinder power and 1 degree in cylinder axis.

Therefore, in a preferred embodiment, refraction system 300 is used to provide prescription of standard precision for conventional eyeglasses and contact lenses. In another preferred embodiment, refraction system 300 is used to provide high precision prescription for custom or premium eyeglasses and contact lenses. In further another preferred embodiment, refraction system 300 has a first software algorithm to provide a first prescription of standard precision for conventional eyeglasses and contact lenses and a second software algorithm to provide a second prescription of high precision for fabricating custom or premium eyeglasses and contact lenses. The second prescription of high precision is preferably to provide in a non-conventional format and is coded and used for a specific lens fabrication process.

Therefore, the integrated refractor of the present invention combines the advantages of an objective auto-refractor and a subjective auto-phoropter. The integrated refractor provides an open-field and binocular viewing to overcome instrument myopia and to mimic viewing experience of a phoropter. Furthermore, the integrated refractor employs a pair of optical trombone to eliminate the need of flipping the trial lenses for defocus power correction. Although aspects of the present invention are described with specific embodiments, various modifications can be made without departing from the scopes of the appended claims.

What is claimed is:

1. A refraction system comprising:
a left viewing unit employed a first viewing path, a first set of folding optics, a first refractor sensor, a first optical relay of unit magnification, and a first cylinder corrector, wherein said first optical relay is constructed as part of said first viewing path and is to change defocus power of said first viewing path, and wherein said first set of folding optics folds said first viewing path to provide a viewing experience mimic to a phoropter, and said first refractor sensor is located to measure refractive errors through said first optical relay of said first viewing path;
a right viewing unit employed a second viewing path, a second set of folding optics, a second refractor sensor, a second optical relay of unit magnification, and a second cylinder corrector, wherein said second optical relay is constructed as part of said second viewing path and is to change defocus power of said second viewing path, and wherein said second set of folding optics folds said second viewing path to provide a viewing experience mimic to a phoropter, and said second refractor sensor is located to measure refractive errors through said second optical relay of said second viewing path; and
a moving mechanism coupled to translate said left viewing unit with respect to said right viewing unit;
wherein said refraction system enables said subject eyes to look through said left and right viewing units and to focus on an external viewing chart positioned at a predetermined distance outside said left and right viewing units, and wherein said refraction system enables both of objective refraction and subjective refraction through said first optical relay and said second optical relay.

2. The refraction system of claim 1, wherein said first refractor sensor and said second refractor sensor are each a Hartmann-Shack wavefront sensor.

3. The refraction system of claim 1, wherein said first optical relay and said second optical relay are each a pair of optical trombones.

4. The refraction system of claim 1, wherein said first optical relay and said second optical relay include each an optical trombone and an afocal relay.

5. The refraction system of claim 1, wherein said left viewing unit and said right viewing unit provide apparently straight viewing paths from said subject eyes to said viewing chart.

6. The refraction system of claim 1, wherein said left viewing unit and said right viewing unit include each a viewing path indicator.

7. The refraction system of claim 1, further comprising:
a system processor including a first software algorithm to provide a first prescription of standard precision for conventional eyeglasses and contact lenses and a second software algorithm to provide a second prescription of high precision in a non-conventional format for fabricating custom or premium eyeglasses and contact lenses, wherein said first and second prescriptions are calculated from measurement data of said refraction system.

8. A method for constructing a refraction system, comprising the steps of:
providing a left viewing unit employed a first viewing path, first set of folding optics, a first refractor sensor, a first optical relay of unit magnification, and a first cylinder corrector, wherein said first optical relay is constructed as part of said first viewing path and is to change defocus power of said first viewing path, and wherein said first set of folding optics folds said first viewing path to provide viewing experience mimic to a phoropter, and said first refractor sensor is located to measure refractive errors through said first optical relay of said first viewing path;
providing a right viewing unit employed a second viewing path, second set of folding optics, a second refractor sensor, a second optical relay of unit magnification, and a second cylinder corrector, wherein said second optical relay is constructed as part of said second viewing path and is to change defocus power of said second viewing path, and wherein said second set of folding optics folds said second viewing path to provide viewing experience mimic to a phoropter, and said second refractor sensor is located to measure refractive errors through said second optical relay of said second viewing path;
providing a moving mechanism coupled to translate said left viewing unit with respect to said right viewing unit; and
providing an external viewing chart positioned at a predetermined distance outside said left and right viewing units;
wherein said subject eyes can look through said left and right viewing units and focus on said viewing chart, and wherein said refraction system enables both of objective refraction and subjective refraction through said first optical relay and said second optical relay.

9. The refraction system of claim 1, wherein said first viewing path includes a first front turning mirror positioned to turn said first viewing path away from its first straight viewing path and a first end turning mirror positioned to return said first viewing path back to said first straight viewing path, and wherein said second viewing path includes a second front turning mirror positioned to turn said second viewing path away from its second straight viewing path and a second end turning mirror positioned to return said second viewing path back to said second straight viewing path.

10. The refraction system of claim 1, wherein said first and second optical relays consist of each a pair of optical relays with complementary magnifications.

11. The refraction system of claim 1, wherein said first and second cylinder correctors consist of each a set of cylindrical lenses.

12. The refraction system of claim 1, wherein said first and second cylinder correctors consist of each a pair of positive and negative cylindrical lenses.

13. The refraction system of claim 1, wherein said first optical delay is driven to change defocus power via a signal from said first refractor sensor, and wherein said second optical delay is driven to change defocus power via a signal from said second refractor sensor.

14. The refraction system of claim 1, wherein said first cylinder corrector is driven to correct cylindrical error via a signal from said first refractor sensor, and wherein said second cylinder corrector is driven to correct cylindrical error via a signal from said second refractor sensor.

15. The refraction system of claim 9, wherein said first end turning mirror is positioned 100 mm or closer from said first front turning mirror, and wherein said second end turning mirror is positioned 100 mm or closer from said second front turning mirror.

16. The refraction system of claim 1, wherein said first optical relay of unit magnification and said second optical delay of unit magnification have each a magnification of +1.

17. The refraction system of claim 1, wherein said predetermined distance outside said left and right viewing units is 20 feet (or 6 meters) for distance visual acuity test and 40 cm for near visual acuity test.

18. A refraction system comprising:
a left viewing unit employed a first viewing path, a first set of folding optics, a first refractor sensor, a first optical relay of unit magnification, and a first cylinder corrector, wherein said first optical relay is constructed as part of said first viewing path and is to change defocus power of said first viewing path, and wherein said first set of folding optics folds said first viewing path to provide a viewing experience mimic to a phoropter, and said first refractor sensor is located to measure refractive errors through said first optical relay of said first viewing path;
a right viewing unit employed a second viewing path, a second set of folding optics, a second refractor sensor, a second optical relay of unit magnification, and a second cylinder corrector, wherein said second optical relay is constructed as part of said second viewing path and is to change defocus power of said second viewing path, and wherein said second set of folding optics folds said second viewing path to provide a viewing experience mimic to a phoropter, and said second refractor sensor is located to measure refractive errors through said second optical relay of said second viewing path; and
a moving mechanism coupled to translate said left viewing unit with respect to said right viewing unit;
an external viewing chart positioned at a predetermined distance outside said left and right viewing units; and
a system processor including a first software algorithm to provide a first prescription of standard precision for conventional eyeglasses and contact lenses and a second software algorithm to provide a second prescription of high precision in a non-conventional format for fabricating custom or premium eyeglasses and contact lenses;
wherein said refraction system enables said subject eyes to look through said left and right viewing units and to focus on said external viewing chart, and wherein said refraction system enables both of objective refraction and subjective refraction through said first optical relay and said second optical relay.

19. The refraction system of claim 18, wherein said external viewing chart is positioned 20 feet (or 6 meters) away from said left and right viewing units, for distance visual acuity test.

20. The refraction system of claim 18, wherein said external viewing chart is positioned 40 cm away from said left and right viewing units, for near visual acuity test.

* * * * *